(12) United States Patent
Hallbeck et al.

(10) Patent No.: US 8,585,734 B2
(45) Date of Patent: Nov. 19, 2013

(54) ERGONOMIC HANDLE AND ARTICULATING LAPAROSCOPIC TOOL

(75) Inventors: M Susan Hallbeck, Lincoln, NE (US); Dmitry Oleynikov, Omaha, NE (US); Kathryn Done, Lincoln, NE (US); Tim Judkins, Lincoln, NE (US); Allison DiMartino, Alexandria, VA (US); Jonathan Morse, Lincoln, NE (US); Lawton N Verner, Towson, MD (US)

(73) Assignee: Board of Regents of University of Nebraska, Lincoln, NE (US)

( * ) Notice: Subject to any disclaimer, the term of this patent is extended or adjusted under 35 U.S.C. 154(b) by 640 days.

(21) Appl. No.: 12/546,404

(22) Filed: Aug. 24, 2009

(65) Prior Publication Data

US 2009/0312605 A1    Dec. 17, 2009

Related U.S. Application Data

(63) Continuation of application No. 11/056,021, filed on Feb. 11, 2005, now abandoned.

(60) Provisional application No. 60/544,286, filed on Feb. 12, 2004.

(51) Int. Cl.
*A61B 17/00*    (2006.01)

(52) U.S. Cl.
USPC ....................................................... 606/205

(58) Field of Classification Search
USPC ......... 606/205–209, 1, 51, 45, 170, 167, 174; 600/564, 131, 146, 147, 149; 128/897, 128/898; 227/175.1–182.1
See application file for complete search history.

(56) References Cited

U.S. PATENT DOCUMENTS

| 3,730,185 A | 5/1973 | Cook et al. |
| 3,888,004 A | 6/1975 | Coleman |
| 4,258,716 A | 3/1981 | Sutherland |

(Continued)

FOREIGN PATENT DOCUMENTS

| DE | 43-00-307 | 7/1994 |
| DE | 296 23 921 | 8/2000 |

(Continued)

OTHER PUBLICATIONS

Novare Surgical Systems, Inc., "EndoLink™ Articulating Instruments," 2005, 1 page.

(Continued)

*Primary Examiner* — Ryan Severson
*Assistant Examiner* — Katherine M Shi
(74) *Attorney, Agent, or Firm* — Fish & Richardson P.C.

(57) ABSTRACT

The present invention relates to a laparoscopic apparatus. The apparatus includes a handle having a body portion, a top surface, opposite bottom surface, a proximal and distal end. The top surface of the base is contoured to compliment the natural curve of the palm. The apparatus further includes a shaft projecting from the distal end of the handle. The shaft has a proximal and distal end. A control sphere is located on the handle. The control sphere can be moved by one or more of a user's fingers to indicate direction. An end effector is located at the distal end of the shaft. The end effector is connected to the control sphere such that movements made to the control sphere control cause movement (articulation) of the end effector.

18 Claims, 5 Drawing Sheets

(56) References Cited

U.S. PATENT DOCUMENTS

| | | | |
|---|---|---|---|
| 4,320,761 A | | 3/1982 | Haddad |
| 4,439,649 A | * | 3/1984 | Cecchi ........................ 200/6 A |
| 4,672,964 A | | 6/1987 | Dee et al. |
| 4,688,555 A | | 8/1987 | Wardle |
| 4,763,669 A | | 8/1988 | Jaeger |
| 4,838,853 A | | 6/1989 | Parisi |
| 4,852,550 A | | 8/1989 | Koller et al. |
| 4,861,332 A | | 8/1989 | Parisi |
| 4,872,456 A | | 10/1989 | Hasson |
| 4,877,026 A | | 10/1989 | de Laforcade |
| 4,880,015 A | | 11/1989 | Nierman |
| 4,940,468 A | | 7/1990 | Petillo |
| 4,978,333 A | | 12/1990 | Broadwin et al. |
| 4,986,825 A | | 1/1991 | Bays et al. |
| 5,024,652 A | | 6/1991 | Dumenek et al. |
| 5,026,387 A | | 6/1991 | Thomas |
| 5,112,299 A | | 5/1992 | Pascaloff |
| 5,133,736 A | | 7/1992 | Bales, Jr. et al. |
| 5,166,787 A | | 11/1992 | Irion |
| 5,174,300 A | | 12/1992 | Bales et al. |
| 5,176,697 A | | 1/1993 | Hasson et al. |
| 5,209,747 A | | 5/1993 | Knoepfler |
| 5,224,954 A | | 7/1993 | Watts et al. |
| 5,254,130 A | | 10/1993 | Poncet et al. |
| 5,258,007 A | | 11/1993 | Spetzler et al. |
| 5,275,615 A | | 1/1994 | Rose |
| 5,281,220 A | | 1/1994 | Blake, III |
| 5,282,806 A | | 2/1994 | Haber et al. |
| 5,282,807 A | | 2/1994 | Knoepfler |
| 5,282,826 A | | 2/1994 | Quadri |
| 5,300,081 A | | 4/1994 | Young et al. |
| 5,308,358 A | | 5/1994 | Bond et al. |
| 5,314,445 A | | 5/1994 | Heidmueller nee Degwitz et al. |
| 5,318,589 A | | 6/1994 | Lichtman |
| 5,330,502 A | | 7/1994 | Hassler et al. |
| 5,350,355 A | | 9/1994 | Sklar |
| 5,350,391 A | | 9/1994 | Iacovelli |
| 5,354,311 A | | 10/1994 | Kambin et al. |
| 5,368,606 A | | 11/1994 | Marlow et al. |
| 5,374,277 A | | 12/1994 | Hassler |
| 5,383,888 A | | 1/1995 | Zvenyatsky et al. |
| 5,403,342 A | | 4/1995 | Tovey |
| 5,405,344 A | * | 4/1995 | Williamson et al. .............. 606/1 |
| 5,474,571 A | | 12/1995 | Lang |
| 5,536,251 A | | 7/1996 | Evard et al. |
| 5,817,119 A | | 10/1998 | Klieman et al. |
| 5,827,323 A | | 10/1998 | Klieman et al. |
| 5,882,294 A | | 3/1999 | Storz et al. |
| 6,443,973 B1 | | 9/2002 | Whitman et al. |
| RE38,335 E | | 11/2003 | Aust et al. |
| 7,131,985 B1 | | 11/2006 | Manhes |
| 7,156,846 B2 | * | 1/2007 | Dycus et al. .................... 606/51 |
| 7,250,027 B2 | | 7/2007 | Barry |
| 2003/0236549 A1 | | 12/2003 | Bonadio et al. |
| 2006/0190027 A1 | | 8/2006 | Downey et al. |

FOREIGN PATENT DOCUMENTS

| | | |
|---|---|---|
| EP | 0 434 793 B1 | 7/1991 |
| EP | 0 434 793 B2 | 7/1991 |
| EP | 577-423 | 1/1994 |
| EP | 0 902 652 | 7/1995 |
| EP | 0 918 489 | 6/1999 |
| EP | 1 366 705 | 12/2003 |
| FR | 2681775 | 4/1993 |
| WO | WO 91/02493 | 3/1991 |
| WO | WO 93/07816 | 4/1993 |
| WO | WO 94/20034 | 9/1994 |
| WO | WO 2005/079333 | 1/2005 |

OTHER PUBLICATIONS

M.A. van Veelen, "Handle for laparoscopic instrument," Medisign Delft Program for research and development of products in Healthcare,: Aug. 20, 1999, 3 pages.

Microline Pentax, "Microline Announces the World's First Reposable Deflexable Instruments," 2009, 1 page.

Novare Surgical Systems, Inc., "RealHand High Dexterity (HD) instruments," Oct. 7, 2009, 1 page.

International Searching Authority, Written Opinion International Application No. PCT/US2005/004517, mailed Nov. 7, 2007, 5 pages.

\* cited by examiner

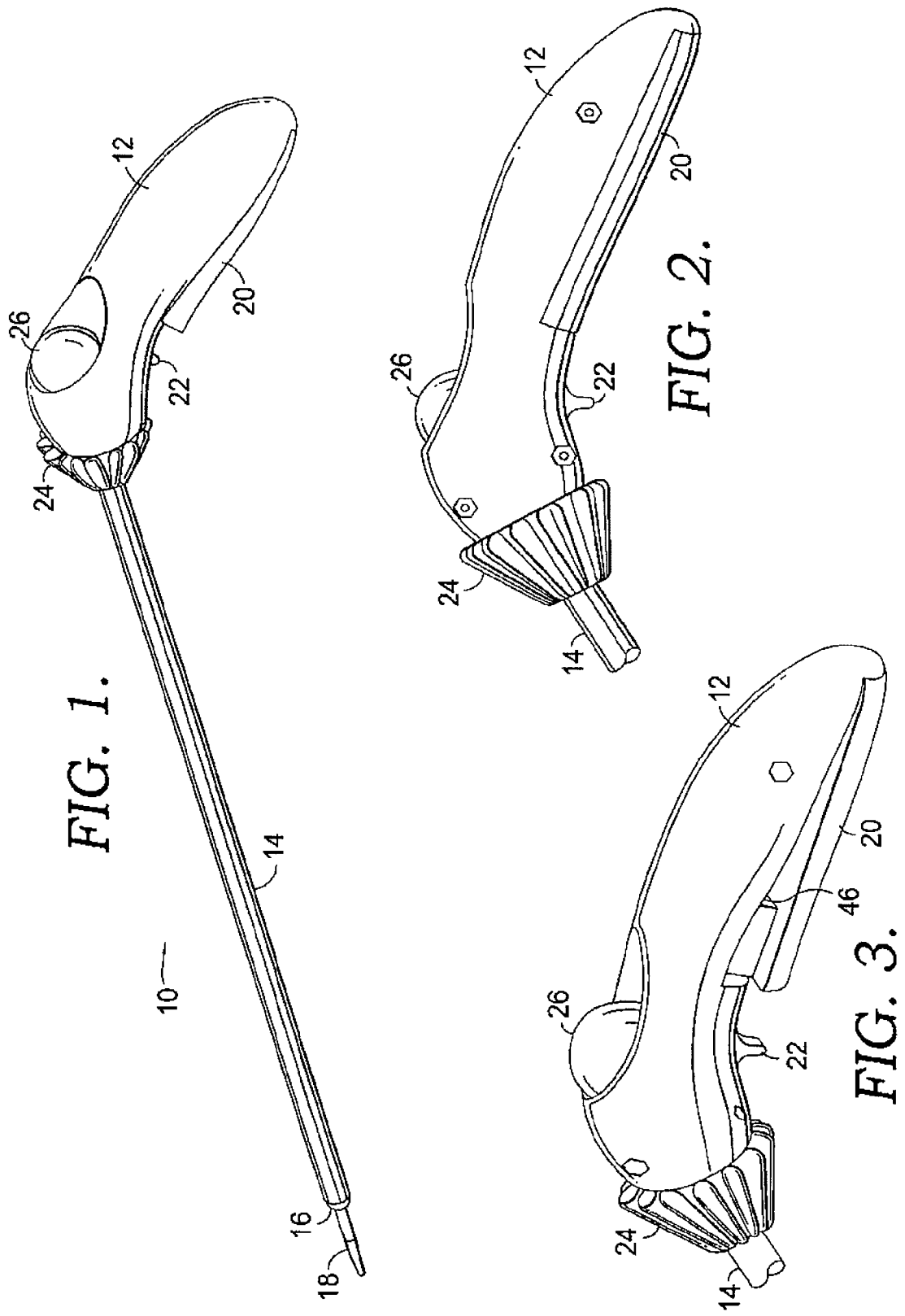

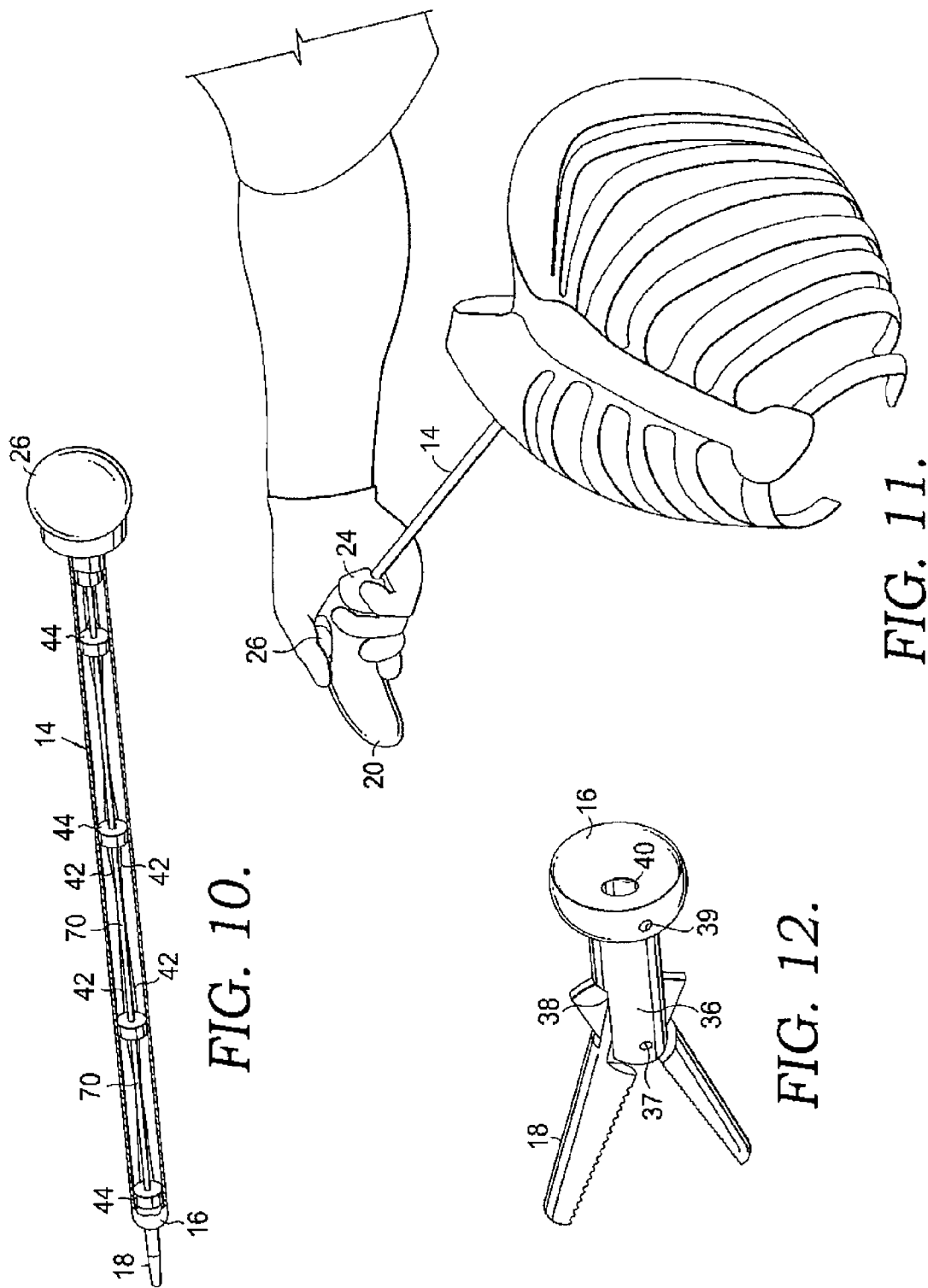

US 8,585,734 B2

ERGONOMIC HANDLE AND ARTICULATING LAPAROSCOPIC TOOL

CROSS REFERENCE TO RELATED APPLICATIONS

This application claims the benefit of priority under 35 U.S.C. §120 to U.S. application Ser. No. 11/056,021 filed Feb. 11, 2005, which claims the benefit of priority to U.S. Provisional Application No. 60/544,286 filed on Feb. 12, 2004, both of which are hereby incorporated by reference in their entirety.

STATEMENT REGARDING FEDERALLY SPONSORED RESEARCH OR DEVELOPMENT

Not applicable.

BACKGROUND

Surgeons have identified and studies have shown, laparoscopic techniques require greater concentration and place greater mental and physical stress on surgeons than open surgery. The tools that laparoscopic surgeons must use are difficult to use and because of suboptimal design, they may actually be doing harm to the highly trained physician. Additionally, poor laparoscopic tools increase physician fatigue, creating potential for errors that may harm the patient.

Specialized instruments are required for laparoscopic surgery due to the small ports. The design of these instruments is critical to the result of the surgery. Current laparoscopic instruments have been found to be very poorly designed ergonomically and it is likely that ergonomics were not considered at all. Some practicing laparoscopic surgeons frequently experience post operation pain or numbness. This is generally attributable to pressure points on the laparoscopic tool handle. Furthermore, four different handle designs used on laparoscopic tools (shank, pistol, axial, and ring handle) have been found to result in either painful pressure spots or caused extreme ulnar deviation.

Compared to general surgery, laparoscopic surgery is a new practice. Therefore, the tools available to perform the procedures are not yet perfected. Limited work has been done by others to improve both the tools and procedures used in laparoscopy; however, an optimized tool, based on task analysis of laparoscopic surgery and sound ergonomic principles has not been prototyped and tested fully to date.

Furthermore, non-ergonomic tool handles often cause pain and discomfort and also result in painful pressure spots. It would be beneficial to have a laparoscopic tool with an ergonomic handle, an intuitive hand/tool interface, such as a control sphere, and an articulating end effector. It would also be beneficial to have an ergonomic tool handle with an intuitive hand/tool interface for use with other types of tools.

SUMMARY

In one embodiment, the present invention relates to a laparoscopic apparatus. The apparatus comprises a handle having a body portion, a top surface, opposite bottom surface, a proximal and distal end and a shaft projecting from the distal end of the handle, the shaft having a proximal and distal end. The apparatus further comprises a control sphere located on the handle and an end effector located at the distal end of the shaft, wherein the end effector is connected to the control sphere such that movements made to the control sphere control movement of the end effector.

In another embodiment, the present invention relates to an ergonomic handle apparatus for use with a tool. The handle apparatus comprises a base having a body portion, a top surface, opposite bottom surface, a proximal and a distal end, where the top surface of the base being contoured to compliment the natural curve of the palm. The handle apparatus further comprises a control sphere located on the base, wherein the control sphere can be moved by one or more of a user's fingers to indicate direction and at least one lever projecting from the bottom surface, wherein the lever may be actuated by a user.

In yet another embodiment, the present invention relates to a laparoscopic apparatus. The apparatus comprises a handle having a body portion, a top surface, opposite bottom surface, a proximal and distal end, where the top surface of the base is contoured to compliment the natural curve of the palm. The apparatus further includes a shaft projecting from the distal end of the handle, the shaft having a proximal and distal end and a control sphere located on the handle. The control sphere can be moved by one or more of a user's fingers to indicate direction. An end effector is located at the distal end of the shaft and the end effector is connected to the control sphere such that movements made to the control sphere control movement of the end effector.

BRIEF DESCRIPTION OF THE DRAWINGS

FIG. 1 is a perspective view of a laparoscopic apparatus in accordance with an embodiment of the present invention;

FIG. 2 is a side perspective view of an ergonomic handle in the closed position in accordance with an embodiment of the present invention;

FIG. 3 is a side perspective view of an ergonomic handle in the open position in accordance with an embodiment of the present invention;

FIG. 10 is side perspective view of a laparoscopic apparatus with a cutaway showing the internal control cables in accordance with an embodiment of the present invention;

FIG. 11 is a view of a reverse use position of a laparoscopic apparatus in accordance with an embodiment of the present invention;

FIG. 12 is an exploded perspective view of an end effector and graspers of a laparoscopic apparatus in accordance with an embodiment of the present invention;

DETAILED DESCRIPTION

Figure 6:
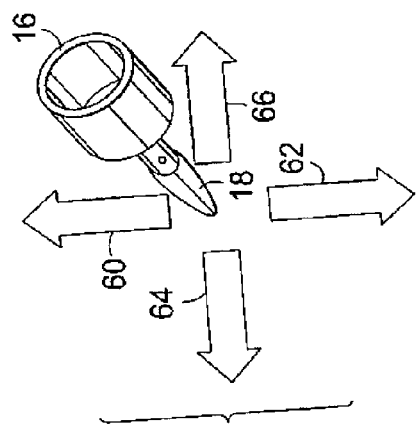
FIG. 6 is an enlarged perspective view of a portion of a laparoscopic apparatus in accordance with an embodiment of the present invention.

With reference to FIG. 1, an ergonomic laparoscopic tool (10) is shown. Laparoscopic tool (10) comprises of five main components: an ergonomic handle (12), several controls, a shaft (14), an articulating end effector (16), and graspers (18). The graspers (18) may be any effectors such as cutting forceps and jawed end effectors or may be powered for cauterizing. The cauterizing may include electrosurgical cutting and coagulation of tissue.

In one embodiment, the shaft (14) is a 10 mm shaft. In this embodiment, the shaft is about 10 mm in diameter and about 40 cm long. The shaft houses the wire guides and actuation cables, described later. However, one of skill in the art will appreciate that the shaft, wire guides and actuation cables are scalable and may be any size, including, but not limited to, about 3 mm and about 5 mm in diameter and about 35-55 cm long.

With reference next to FIG. 2, the tool handle (12) is a smooth, contoured shape. It is designed ergonomically for comfort and usability. In one embodiment, the handle (12) is about 155 mm (length) by about 35 mm (height) by about 45 mm (width). In another embodiment, the handle (12) may be about 150-165 mm in length, about 30-40 mm in height and about 40-50 mm in width. The handle has a top and bottom surface and a proximal and distal end. The proximal end of the handle is located nearest a user and the distal end is the end located farthest from a user. The top surface of the handle is contoured to compliment the natural curve of the palm.

In one embodiment, the handle circumference is about 5 cm and tapered in shape. A preferred range of handle circumference is from about 4 cm to 6.5 cm. The distal end of the handle is also curved such that the tool shaft (14) is angled at about 135 degrees to increase the accuracy of pointing with the tool. However, the distal end of the handle may be curved to at any variety of angles depending on the tool that the handle is used with. The handle is designed to fit hand sizes ranging from about the 5th percentile female to about the 95th percentile male. The tool handle is described in relation to a laparoscopic instrument, however, it will be appreciated that the ergonomic tool handle (12) may be used with any variety of tools including a homeland security device, such as a sensing device, or a laser pointer for presentations.

The handle (12) is designed for comfortable use with three different hand orientations. The first hand position is such that the thumb controls the sphere, and the fingers are wrapped around the handle and squeeze the grip (20). The second hand position uses the thumb to squeeze the grip (20), and the fingers are wrapped across the top of the handle (12) with the index finger controlling the sphere (26). The third is a reverse grip shown in FIG. 11. In the reverse position, the fingers are wrapped around the handle (12) so that the index finger squeezes the grip (20), the control sphere (26) is moved with the user's thumb and the collet mechanism (24) is controlled with the user's pinky finger. The collet mechanism (24) may include a swivel collet or rotating grip. The first two positions allow comfortable control of the tool without straining a user's arm, wrist, or fingers. And the third reduces the reach and awkward postures that many users, such as surgeons, encounter while performing their tasks, especially from a reverse position.

Referring next to FIG. 3, there are six controls located on the tool handle (12) including a squeeze grip (20), slip lock trigger (22), a collet mechanism (24), a control sphere (26), and sphere lock (28). In one embodiment, the controls are placed so they are reachable by the thumb or index finger. However, it will be appreciate that the tool handle (12) may be used in a variety of ways such that the controls can be reached by other fingers.

The squeeze grip (20) actuates the graspers (18) at the end of the tool (10). When the grip (20) is squeezed closed, the graspers (18) close (the closed position is shown in FIG. 2). The grip (20) is sprung such that when released the graspers (18) will open if the slip lock is disengaged (the open position is shown in FIG. 3). In one embodiment, the grip pivots (46) are located toward the distal end of the handle such that the stronger, more dexterous index and middle fingers can squeeze the grip in some of the grip positions. In one embodiment, the pivot angle between the body of the handle and the squeeze grip (20) when the squeeze grip is open is about 4-18 degrees, preferably about 17 degrees and the pivot angle when the squeeze grip is closed is about 0 degrees.

Figure 4:
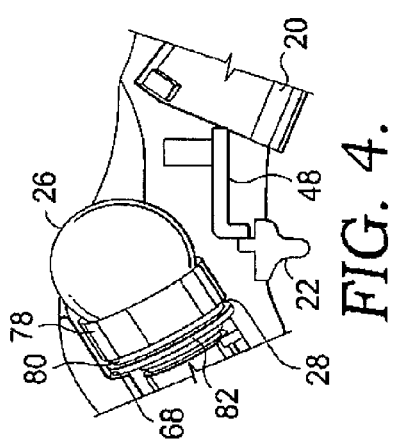
FIG. 4 is a longitudinal cross sectional view of an ergonomic handle with a slip lock in accordance with an embodiment of the present invention.
Figure 5:
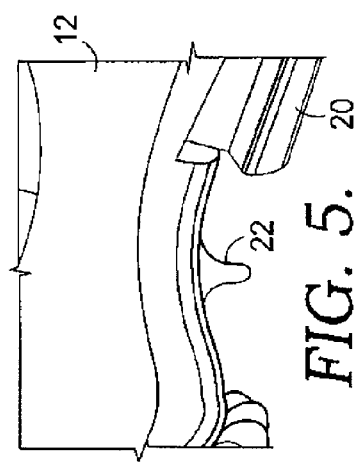
FIG. 5 is an enlarged side perspective view of an ergonomic handle in accordance with an embodiment of the present invention.

With reference to FIGS. 4 and 5, in one embodiment, when the squeeze grip (20) is closed (as shown in FIG. 2), a slip lock (48) prevents the squeeze grip (20) from opening. A ratcheting mechanism is used to perform this action. However, one of skill in the art will appreciate that any variety of mechanisms or methods may be used to prevent the squeeze grip (20) from opening. The slip lock (48) allows smooth motion while still preventing the squeeze grip (20) from reopening. The slip lock trigger (22) will disengage the slip lock (48), allowing the squeeze grip (20) to open. The slip lock trigger (22) locks in position when pulled back disengaging contact between the slip lock (48) and squeeze grip (20). In one embodiment, the slip lock (48) is located about 2-3 cm, preferable, about 2.7 cm, from the collet mechanism (24) and is substantially centered along the lateral axis of the handle (12). In this embodiment, the actuation force needed to for the sliplock (48) to rotate the shaft (14) is between about 0.5 and 1.0 lbs, preferably about 0.6 lbs.

With reference to FIG. 6, a collet mechanism (24) is located on the front of the handle (12). When rotated, a collet mechanism (24) turns the end effector (16) about the axis of the tool shaft (14). The collet mechanism (24) is free to rotate 360 degrees. In one gripping position, the collet mechanism (24) is reached with the index finger for one-handed operation. However, depending on the grip position, the collet mechanism (24) may be reached with a user's thumb or other finger.

Figure 8:
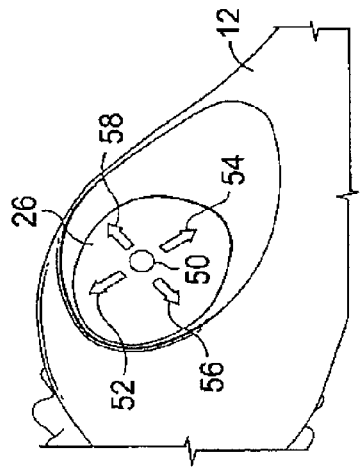
FIG. 8 an enlarged perspective view of graspers of a laparoscopic apparatus in accordance with an embodiment of the present invention.
Figure 7:
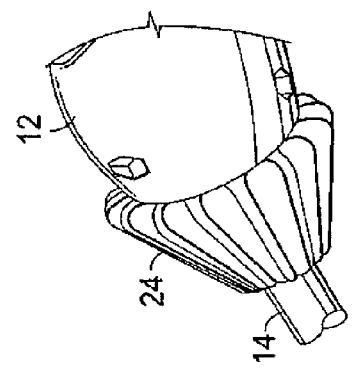
FIG. 7 is top perspective view of a control sphere of an ergonomic handle in accordance with an embodiment of the present invention.

With reference to FIGS. 1, 7 and 8, the control sphere (26) actuates the pitch and yaw of the end effector (16). The control sphere (26) can also be used to rotate to end effector (16) in the same manner as the collet mechanism (24). A small tactile element (50) on the top the sphere (26) aligns with the tool shaft (14) when the end effector (16) is aligned with the shaft (14). The tactile element (50) provides a sense of touch for location of the end effector (16). The tactile element (50) is an inward element or an outward bump to orient a user as to the position of articulation. Control is intuitive where moving the tactile element (50) forward/up (52) moves the tip of the end effector up (60), and moving the tactile element (50) backward/down (54) moves the end effector down (62). Likewise, moving the tactile element (50) left (56) or right (58) moves the end effector left (64) or right (66), respectively.

In one embodiment, the control sphere is located in at or near the center of the lateral axis of the handle and about 3-4 cm from the collet mechanism (24). In one embodiment, the control sphere is located about 3.6 cm from the collet mechanism (24) and is substantially inline with the shaft (14). In this embodiment, the actuation force needed to move the control sphere such that it moves the end effector properly between about 2 and 5 lbs, preferably about 3 lbs.

With reference to FIG. 4, the sphere lock (28) is an internal mechanism involving a wave spring (82). When in the released position, the wave spring (82) pushes the control sphere (26) into contact with the inside of the handle shell (68) which locks the sphere (26) in place which in turn prevents articulation of the end effector (16). Also, because the sphere (26) and collet mechanism (24) both rotate the shaft (14), the sphere lock (28) prevents rotation of the end effector (16) but allows independent rotation of the shaft while the end effector remains in the locked position. When the control sphere (26) is depressed, the wave spring (82) is flattened and the control sphere (26) is released, leaving it free to move. The sphere lock (28) allows the articulating end effector (16) to be placed in one position and the digit (thumb or finger) removed from the sphere (26) which locks the articulation in place. To move the articulating end effector (16), pressure from the digits is required. Thus, the articulation is stationary once the sphere (26) is not under digital pressure and can move freely once unlocked, after the digit (thumb or finger) engages the control sphere (26).

With reference to FIG. 12, in one embodiment the actuating end effector (16) is based on a spherical shape. It will be appreciated that the articulating end effector may take any shape, however. The spherical end effector (16) may be of any size proportional to the graspers (18) and shaft (14). In one embodiment, the end effector (16) is approximately about 10 mm in diameter, scaled to the size of the shaft (14). Attached to the front of the spherical end effector (16) is a protrusion with two wings (36) that hold the graspers (18) via a pin (37). Small wings (36), similar to those found on the current rigid tools, are attached to the spherical end effector (16) to hold the graspers' (18) pivot point from the end effector's (16) center. A slot (38) between the wings (36) is also used to allow grasper movement.

In one embodiment, a portion of the spherical end effector (16) is removed leaving approximately ½-¾ of a sphere. However, it can be appreciated that different amounts of a spherical end effector may be removed. A small hole (40) extends through the end effector to allow the grasper cable to pass. In the embodiment having a spherical end effector (16) that is approximately about 10 mm in diameter, the small hole (40) is approximately about 2 mm in diameter. The spherical end effector (16) is split across the equator for attachment of control cables (42) described in more detail below. Four attachment mechanisms, such as screws, hold the end effector (16) together and secure the control cables (42) to the end effector (16).

With reference to FIG. 10, the pitch and yaw of the end effector (16) are actuated by the control sphere (26). In one embodiment, four inextensible control cables (42) connect the control sphere through the shaft (14) to the end effector (16). It will be appreciated that the control cables may be wires or the like and that any number of control cables may be used to connect the control sphere (26) to the end effector (16). The control cables are fed through four wire guides (44) internal to the shaft (14) to prevent end-effector (16) and control sphere (26) from having shaft-independent rotation.

In one embodiment, the control sphere (26) is about three times larger than the end effector (16). For example, if the spherical end effector (16) is about 10 mm in diameter, the control sphere (26) is about 30 mm diameter. The difference in size enables the user to have more precise control over the end effector (16). Also, in one embodiment, the control sphere (26) is in-line with the actuating effector (16).

In one embodiment, the control cables (42) running through the shaft (14) are rotated a total of about 180° when passed through the wire guides (44). This rotation ensures that when the control sphere (26) is moved left, the end effector (16) will move left, and when the control sphere (26) is moved forward, the end effector (16) will move up.

The four control cables (42) have swaged balls attached to each end. In the embodiment with an end effector (16) having a diameter of about 10 mm, the swaged balls and each end of the four control cables (42) are approximately about 2 mm. Both the end effector and control sphere are split along their equators. The swaged ends of the control cables (42) seed into depressions (39) in each hemisphere of the end effector (16). Four attachment mechanisms, such as screws, hold the two hemispheres of the end effector (16) together and secure the control cables (42). The control cables (42) connect to the control sphere (26) also seed into depressions (37) in the control sphere (26). One attachment mechanism, such as a screw, holds the top half of the control sphere (26) in place and secures the control cables (42). A screw cover may be used to hide the screw and has a small tactile element for tactile feedback.

The tool shaft (14) is able to rotate 360°. Normally, rotation of the control ball would cause the control cables to become tangled; consequently, control of the end effector (16) would be lost. The tool (10) allows the shaft (14) and actuating end effector (16) (along with the cables (42)) to rotate about the tool handle (12) without becoming entangled.

With continued reference to FIG. 10, the graspers (18) are opened and closed by the movement of an actuator rod (70) located within shaft (14). The internal mechanism was designed to allow an external forward and backward movement to control the graspers (18), while allowing rotation that does not twist or bind the internal control cables (42). The actuator rod (70) extends through the shaft (14) and wire guides (44). At the control sphere (26) end, two halves of a pull cylinder (72) are connected to the actuator rod (70) by two pins that extend through the actuator rod (70) perpendicular the axis of the actuator rod (70). The pull cylinder (72) is free to move forward and backward along the shaft (14). At the actuating end, a flexible cable (not shown) extends from the shaft and connects to an eyelet that opens and closes the graspers (18) when the actuator rod (70) moves forward and backward. When the pull cylinder (72) is moved back toward the control sphere (26), the graspers (18) close. When the pull cylinder (72) is pushed forward, the graspers (18) open.

Figure 9:
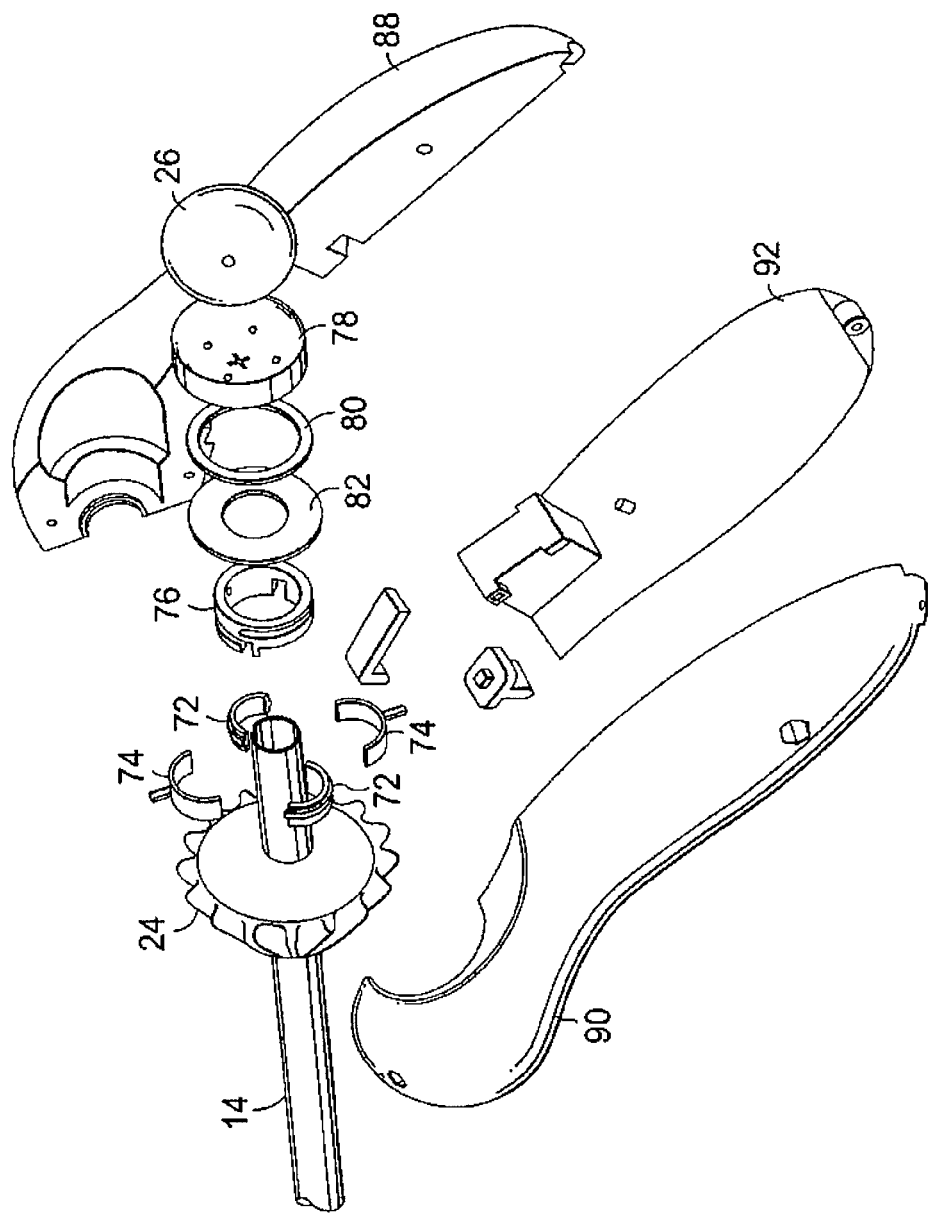
FIG. 9 is a perspective view of an ergonomic handle used with a laparoscopic apparatus displaying the internal components in accordance with an embodiment of the present invention.

With reference to FIG. 9, four-piece assembly of cylinder (72) allows the pull cylinder (72) to rotate with the shaft (14) while the outer covers (74) are stationary. A rotary cylinder (76) slides over the outer covers (74) such that the posts on the outer covers (74) feed through inclined tracks on the rotary cylinder (76). When the rotary cylinder (76) is turned, the outer covers (74) are forced forward and backward actuating the graspers (18). The control sphere (26) rests in a cradle (78) that has four ball bearings embedded in it for smooth operation. Extending from the bottom of the cradle (78) is a short shaft (not shown) that mates with the shaft (14) of the tool (10). This maintains the rotation of the control sphere (26) with the end effector (16) so the control cables (42) do not become tangled. A TEFLON bearing (80) allows the cradle (78) to rotate smoothly with the shaft (14) and a wave spring (82) for the sphere lock (28).

Figure 13:
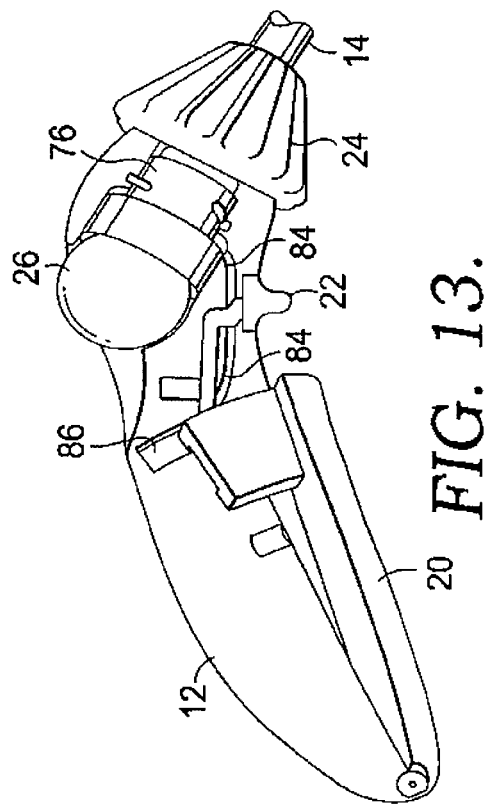
FIG. 13 is a side perspective view of an internal portion of the ergonomic handle in accordance with an embodiment of the present invention.
Figure 14:
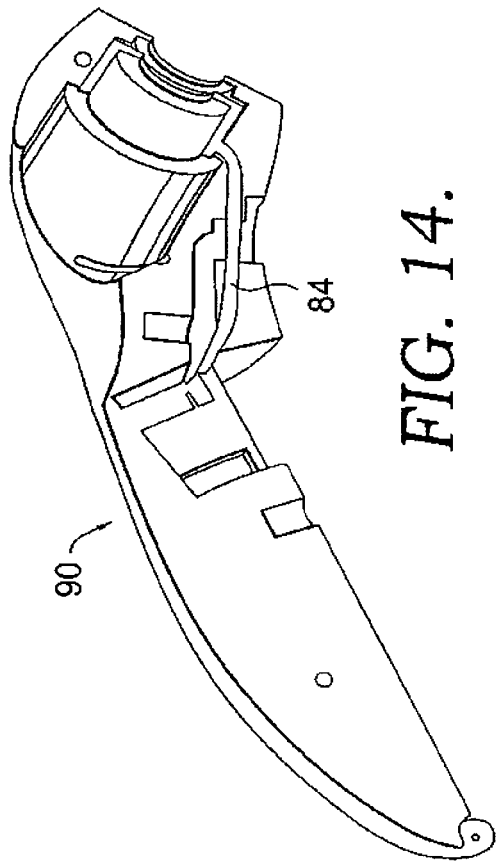
FIG. 14 is a side perspective view of the internal portion of a left half of an ergonomic handle in accordance with an embodiment of the present invention.

With reference to FIG. 13, rotary cylinder (76) is connected to the squeeze grip (20) by an actuating cable (not shown). It will be appreciated that the actuating cable may be any type of cable including a pull cable and push-pull cable. The cable has two swaged ball ends that fit into a protrusion (86) on the squeeze grip (20) and a recess on the rotary cylinder (76). The cable runs through a groove (84) in the left side of the handle (90). The squeeze grip (20) is spring-loaded such that the graspers (18) open when the squeeze grip (20) is released.

The handle (12) can comprise multiple components or may be one component. In one embodiment, the handle (12) comprises a right half of handle (88), left half of handle (90) and a handle grip (90). One of skill in the art will appreciate that the handle (12) may be made up of any number of components or may be a unitary handle.

From the foregoing, it will be seen that this invention is one well adapted to attain all the ends and objects hereinabove set forth together with other advantages which are obvious and which are inherent in the structure. It will be understood that certain features and subcombinations are of utility and may be employed without reference to other features and subcombinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

The invention claimed is:

1. A laparoscopic apparatus, the apparatus comprising:
   a handle having a body portion, a top surface, an opposite bottom surface, a proximal and distal end;
   a shaft projecting from the distal end of the handle, the shaft having a proximal and distal end;
   an end effector located at the distal end of the shaft;
   a control sphere located on the handle opposite from the shaft, the control sphere being movable with multiple degrees of freedom relative to the handle so as to actuate both pitch and yaw motions of the end effector, wherein the pitch of the end effector is changed when the control sphere is moved upward and downward relative to the handle, and wherein the yaw of the end effector is changed when the control sphere is moved right and left relative to the handle; and
   a collet rotatable about a longitudinal axis of the shaft, wherein rotation of the collet mechanism drives rotation of the shaft relative to the handle, wherein the end effector and the control sphere rotate with the shaft relative to the handle.

2. The apparatus of claim 1, wherein the control sphere rests within a cradle that rotates when the shaft rotates relative to the handle.

3. The apparatus of claim 1, wherein the control sphere is located about 3 to 4 centimeters from the collet mechanism and is in line with the shaft.

4. The apparatus of claim 1, wherein the end effector comprises a spherical surface that extends outward from the distal end of the shaft and further comprises two wings that retain movable graspers therebetween.

5. The apparatus of claim 4, further comprising a squeeze grip lever movably arranged on the bottom surface of the handle so as to actuate an elongate rod in the shaft that adjusts the graspers between an opened position and a closed position.

6. The apparatus of claim 4, wherein the diameter of the control sphere is about three times larger than the diameter of the spherical surface of the end effector.

7. The apparatus of claim 1, further comprising:
   a tactile element at the top of the control sphere that aligns the control sphere with the shaft.

8. The apparatus of claim 7, wherein the pitch of the end effector is moved upward when the tactile element on the control sphere is moved upward, the pitch of the end effector is moved downward when the tactile element on the control sphere is moved downward, the yaw of the end effector is moved right when the tactile element on the control sphere is moved right, and the yaw of the end effector is moved left when the tactile element on the control sphere is moved left.

9. The apparatus of claim 1, wherein the change is in the same direction relative to the movement of the control sphere.

10. The apparatus of claim 1, wherein the change is in the opposite direction relative to the movement of the control sphere.

11. An ergonomic handle apparatus for use with a tool, the handle comprising:
   a tool shaft having a proximal and a distal end;
   a base having a body portion, a top surface, an opposite bottom surface, a proximal and a distal end, the top surface of the base having a convex contour to complement a palm and the distal end receives the proximal end of the tool shaft, the distal end of the tool shaft configured to receive a tool;
   a control sphere arranged along the top surface of the base and movable relative to the base so as to manipulate the tool, wherein the control sphere is rotatable about a first axis to provide multiple degrees of freedom in a first axis relative to the base and adjust a pitch orientation of the tool and is rotatable about a second axis to provide multiple degrees of freedom in a second axis relative to the base and adjust a yaw orientation of the tool, wherein the pitch of the tool is moved back and forth when, respectively, the control sphere is moved back and forth in the first axis, and wherein the yaw of the tool is moved back and forth when, respectively, the control sphere is moved back and forth in the second axis;
   a rotatable knob coaxial with the shaft, wherein rotation of the rotatable knob drives rotation of the shaft relative to the base, wherein the control sphere rotates with the shaft relative to the base; and
   at least one lever projecting from the bottom surface, wherein the lever is hingedly movable relative to the base so as to manipulate the tool.

12. The handle apparatus of claim 11, wherein the at least one lever has a pivot point located toward the distal end of the handle.

13. The handle apparatus of claim 12, wherein the at least one projecting lever is a squeeze grip, wherein the squeeze grip is open about 4 to 18 degrees from the bottom surface of the base when it is not actuated by a user, and wherein the squeeze grip is open 0 degrees from the bottom surface of the base when actuated by a user.

14. The handle apparatus of claim 11, wherein the control sphere is arranged along the top surface of the base such that the control sphere is accessible to a user's thumb while the user grips the lever projecting from the bottom surface.

15. The handle apparatus of claim 11, wherein the handle circumference is between about 4 cm and about 6.5 cm, the handle length is between about 150 and 165 mm, and the handle width is between about 40 and 50 mm.

16. The handle apparatus of claim 11, wherein the distal end of the base is curved such that the tool shaft is angled at about 135 degrees from a longitudinal axis of the base.

17. The apparatus of claim 11, wherein the control sphere rests within a cradle that rotates when the shaft rotates relative to the base.

18. A laparoscopic apparatus, the apparatus comprising:

a handle having a body portion, a top surface, opposite bottom surface, a proximal and distal end, the top surface of the base being contoured to complement the natural curve of the palm;

a shaft projecting from the distal end of the handle, the shaft having a proximal and distal end;

an articulating end effector located at the distal end of the shaft, wherein the end effector comprises graspers attached thereto;

a collet rotatable about a longitudinal axis of the shaft, wherein rotation of the collet mechanism drives rotation of the shaft relative to the handle;

a squeeze grip lever extending from the bottom surface of the handle that actuates an elongate rod in the shaft to open and close the graspers; and a control sphere movably mounted to the handle opposite of the shaft, wherein the control sphere is rotatable about a first axis to provide a first degree of freedom relative to the handle and adjust a pitch orientation of the end effector, and wherein the control sphere is rotatable about a second axis to provide a second degree of freedom relative to the handle and adjust a yaw orientation of the end effector, wherein the pitch of the tool is moved upward when the control sphere is moved upward, the pitch of the tool is moved downward when the control sphere is moved downward, the yaw of the tool is moved right when the control sphere is moved right, and the yaw of the tool is moved left when the control sphere is moved left, wherein the control sphere and the end effector rotate with the shaft relative to the handle.

* * * * *

UNITED STATES PATENT AND TRADEMARK OFFICE
CERTIFICATE OF CORRECTION

| | | |
|---|---|---|
| PATENT NO. | : 8,585,734 B2 | Page 1 of 1 |
| APPLICATION NO. | : 12/546404 | |
| DATED | : November 19, 2013 | |
| INVENTOR(S) | : Hallbeck et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 766 days.

Signed and Sealed this
Fifth Day of May, 2015

Michelle K. Lee
*Director of the United States Patent and Trademark Office*